Figure 3A:
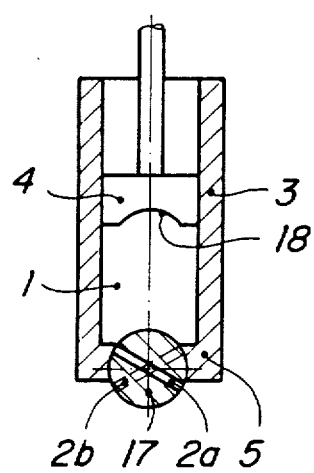

United States Patent [19]

Kaempf et al.

[11] Patent Number: 4,715,237
[45] Date of Patent: Dec. 29, 1987

[54] PROCESS AND APPARATUS FOR QUANTITATIVE AND/OR QUALITATIVE ANALYSIS OF LIQUIDS

[75] Inventors: Karl Kaempf; Paul Zaehner; Wolfgang Richter, all of, Herisau, Switzerland

[73] Assignee: Metrohm AG

[22] PCT Filed: Jul. 1, 1985

[86] PCT No.: PCT/CH85/00105
 § 371 Date: Feb. 12, 1986
 § 102(e) Date: Feb. 12, 1986

[87] PCT Pub. No.: WO86/00703
 PCT Pub. Date: Jan. 30, 1986

[30] Foreign Application Priority Data

Jul. 6, 1984 [CH] Switzerland .......................... 3280/84
Mar. 18, 1985 [CH] Switzerland .......................... 1188/85
Jul. 1, 1985 [WO] PCT Int'l Appl. .......... PCT/CH85/00105

[51] Int. Cl.⁴ .............................................. G01N 1/14
[52] U.S. Cl. ................. 73/864.62; 73/864.63; 73/864.81; 422/100
[58] Field of Search ............... 73/864, 864.01, 864.11, 73/864.13, 864.16, 864.21, 864.22, 864.34, 864.35, 864.51, 864.62, 864.63, 864.64, 864.81, 864.83, 864.84, 863.83, 863.84, 432 B; 324/438; 422/100

[56] References Cited

U.S. PATENT DOCUMENTS

| 744,123 | 11/1903 | Spietschka | 73/863.84 |
|---|---|---|---|
| 3,489,525 | 1/1970 | Natelson | 73/864.81 |
| 3,789,670 | 2/1974 | Rosenwald | 73/864.62 |
| 3,793,886 | 2/1974 | Rosenwald | 73/864.62 |
| 3,793,888 | 2/1974 | Rosenwald | 73/864.62 |
| 3,831,618 | 8/1974 | Liston | 73/864.22 |
| 4,108,602 | 8/1978 | Hanson et al. | 73/864.11 |
| 4,333,356 | 6/1982 | Bartels et al. | 73/864.34 |
| 4,346,742 | 8/1982 | Chase et al. | 73/864.16 |
| 4,406,171 | 9/1983 | Ueberschaer | 73/864.51 |
| 4,413,534 | 11/1983 | Tomoff et al. | 73/864.21 |
| 4,448,752 | 5/1984 | Banno et al. | 73/864.21 |
| 4,461,998 | 7/1984 | Kater | 324/438 |

FOREIGN PATENT DOCUMENTS

| 371496 | 3/1923 | Fed. Rep. of Germany . | |
|---|---|---|---|
| 0824569 | 12/1951 | Fed. Rep. of Germany | 73/863.83 |
| 0498672 | 1/1920 | France | 73/864 |
| 1599716 | 8/1970 | France . | |
| 1481521 | 8/1977 | United Kingdom . | |
| 2025065 | 1/1980 | United Kingdom . | |

Primary Examiner—Michael J. Tokar
Assistant Examiner—Robert R. Raevis
Attorney, Agent, or Firm—Toren, McGeady & Associates

[57] ABSTRACT

The chamber (1) of the metering apparatus is defined by the inside wall surface of a cylinder (3), by a displaceable piston (4), and by a cylinder end portion (5) which is displaceable relative to the cylinder (3). Ducts (2a, 2b) are arranged in the cylinder end portion (5) in such a way that they can be selectively communicated with the chamber (1) or closed off by the end face (7) of the cylinder (3) In that way a part of the chamber wall acts directly as a shut-off member so that no residual volumes remain, which cannot be ejected by the piston (4).

1 Claim, 11 Drawing Figures

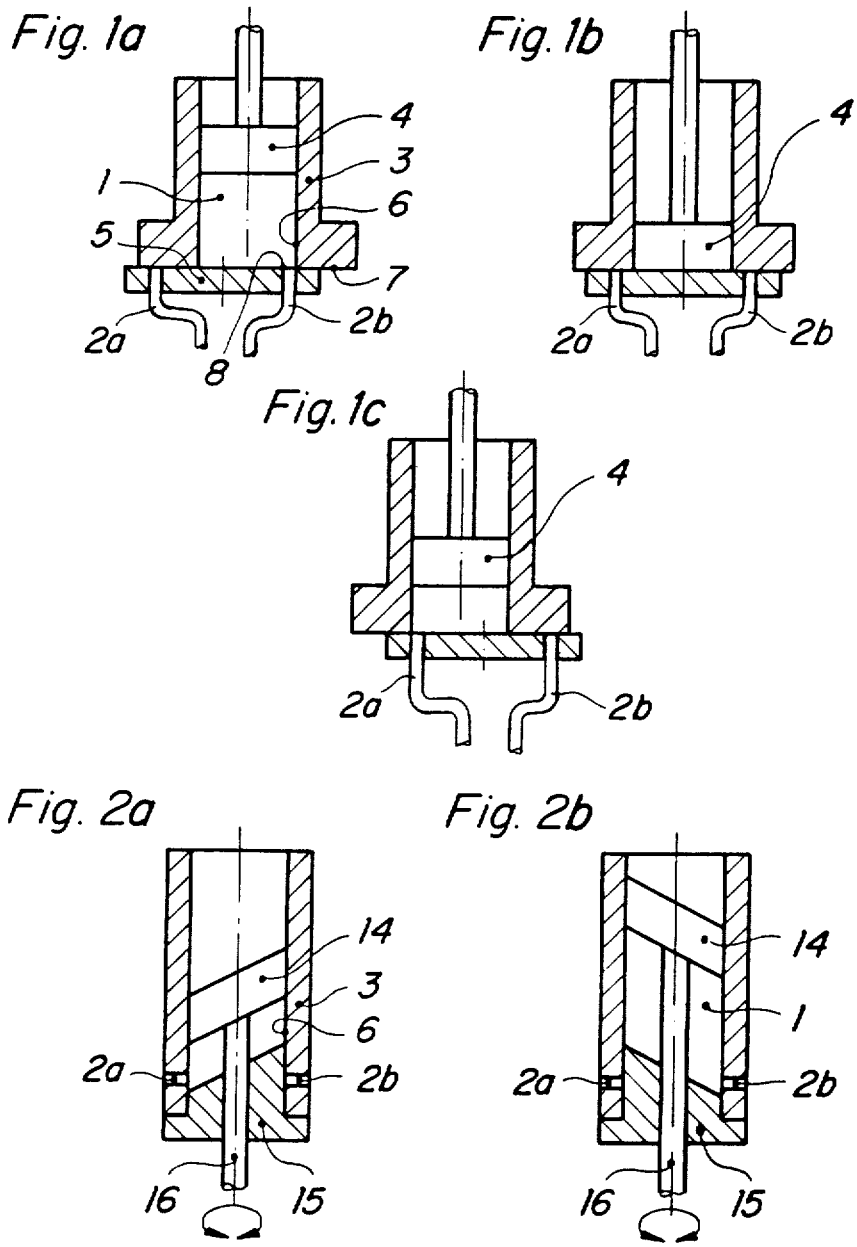

PROCESS AND APPARATUS FOR QUANTITATIVE AND/OR QUALITATIVE ANALYSIS OF LIQUIDS

The invention relates to an apparatus as set forth in the classifying portion of claim 1. Apparatuses of that kind are used inter alia in volumetric analysis. Conventional constructions are for example piston burettes, as are described for example in EP-A-96 088. The piston can be actuated manually or by way of an auxiliary drive. A precise indication of the volume in the chamber in dependence on the position of the piston is nowadays generally provided electronically.

EP-A-1137 discloses a burette-like apparatus in which a cylinder chamber can be increased in size in a stepwise fashion by actuation of a piston or plunger, while various connecting lines can be selectively short-circuited to the chamber. Qualitative analysis of the liquid is effected by ejection into a reaction measuring chamber outside the cylinder chamber.

All known piston burettes suffer from the disadvantage that the chamber volume thereof cannot be increased in size starting from zero and that it is not possible for the entire chamber content to be forced out of the chamber. That is linked to the fact that, even when the apparatus has valves or taps which are arranged directly on the chamber, there always remains a space from which liquid cannot be ejected with the piston. Depending on the purpose of use of the burette, that residual amount may have a detrimental effect on the measurement result in qualitative and quantitative respects. That is an aspect of significance particularly when the chamber of the burette itself is used directly as a reaction chamber. So that in that respect the chamber can be filled in a given sequence with various reagents, and auxiliary and measuring solutions, or can be flushed out in a similar manner, it is absolutely necessary for precisely definable quantities to pass into the chamber while, upon ejection of the liquid, it is essential that no residual amounts should remain in the chamber, which would adversely affect a subsequent measurement operation.

It is therefore an object of the present invention to provide an apparatus of the kind set forth in the opening part of this specification, in which the chamber can be increased in size starting from zero and which can be completely emptied out without a residual amount remaining behind. A further object of the present invention is for as many ducts as possible to be taken into the chamber in a simple fashion from the design point of view, which ducts can be selectively connected to the chamber in such a way that, on changing from one duct to another, no residual amounts of liquids, which cannot be registered by the measuring device, remain in the chamber. In addition the invention seeks to make it possible easily to automate quantitative and/or qualitative analysis operations of that kind.

According to the present invention, that object is attained by an apparatus having the features recited in the characterizing portion of claim 1.

By virtue of wall portions of the chamber itself being formed as a shut-off or closure member, a given amount of liquid can be accommodated by the chamber, starting from a zero chamber volume, in a surprisingly simple fashion, and it is possible to change from a first liquid to a second liquid without an uncontrollable residual amount of the first liquid remaining behind in the chamber. That principle may be embodied in a particularly advantageous manner if the chamber is formed by a cylinder in which a piston is disposed for varying the volume of the chamber, and if the shut-off member is formed by a wall portion which is disposed at the cylinder end and which is displaceable relative to the cylinder casing. In that way the shut-off member may be actuated with the piston in any position. When the piston bears against the cylinder end portion, then the volume of the chamber is equal to zero. When the piston is moved away from the cylinder end portion, then each position of the piston exactly corresponds to a precisely definable amount of liquid in the cylinder, more specifically even when the shut-off member is closed or when a change is made from one duct to another. The term piston is used to indicate in certain situations of use a rotary piston with which the volume of a chamber may be varied by a rotary movement, based on the known principle of the Wankel engine.

Depending on the design configuration selected, the openings of the ducts which open into the chamber may be arranged in the displaceable wall portion at the cylinder end or in the cylinder casing. However a particularly simple design is provided if the displaceable wall portion is the entire cylinder end portion which bears sealingly against the end face of the cylinder casing and if the openings can be closed by the end face of the cylinder casing. In that way the surface to be sealed off is formed as a planar surface, which quite substantially simplifies production of the sealing surface. The end face of the cylinder can easily be formed as an annular surface which is of sufficient width to cover over a connecting opening.

That construction makes it possible in a particularly simple manner to provide a plurality of openings at the cylinder end portion, which openings are associated with various ducts, without large relative movements as between the cylinder end portion and the cylinder casing or the end face of the cylinder casing being necessary in order to connect individual ducts to the chamber.

The apparatus may be mechanically actuated and automated in a particularly advantageous fashion if the cylinder end portion is a circular disc which is disposed in plane-parallel relationship in a control disc in such a way that the control disc is rotatable about the circular disc, if the control disc is connected to a rotary ring non-rotatably relative thereto but displaceably in the plane of the circular disc, and if the control disc together with the circular disc is displaceable by a wedge-action or cam disc which engages the control disc and which for the purposes of positioning the control disc is rotatable about the axis of the cylinder together with the rotary ring and for the purposes of displacing the circular disc is rotatable about the axis of the cylinder separately with the rotary ring stationary. In that way the cylinder end portion may be moved from a neutral position in which all openings are closed by the end face of the cylinder casing, into a predeterminable eccentric position in which one of the openings is open to the chamber.

Motorized drive for the apparatus is provided in a particularly simple manner by virtue of the rotary ring and the wedge-action disc having an external tooth configuration so that they can be individually driven in rotation by way of a gear drive. An extremely precise sealing effect at the cylinder end portion is provided if the cylinder casing and the cylinder end portion are produced from a ceramic material or another suitable material such as for example silicon carbide or sintered material. Those materials may be machined with a very high degree of precision and are also substantially chemically resistant.

A very high degree of versatility of use of the apparatus can be achieved if at least one sensor for qualitative analysis of the liquid is arranged in the interior of the chamber. In that connection it is only necessary to ensure that the sensor arrangement does not give rise to a dead space in the chamber.

The invention also relates to a process for qualitative and/or quantitative analysis of liquids, which is characterised by the features in claim 12.

Figure 3B:
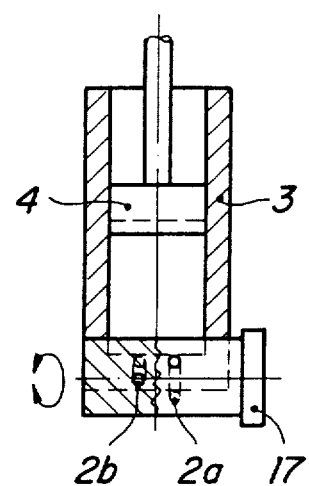
Figure 4:
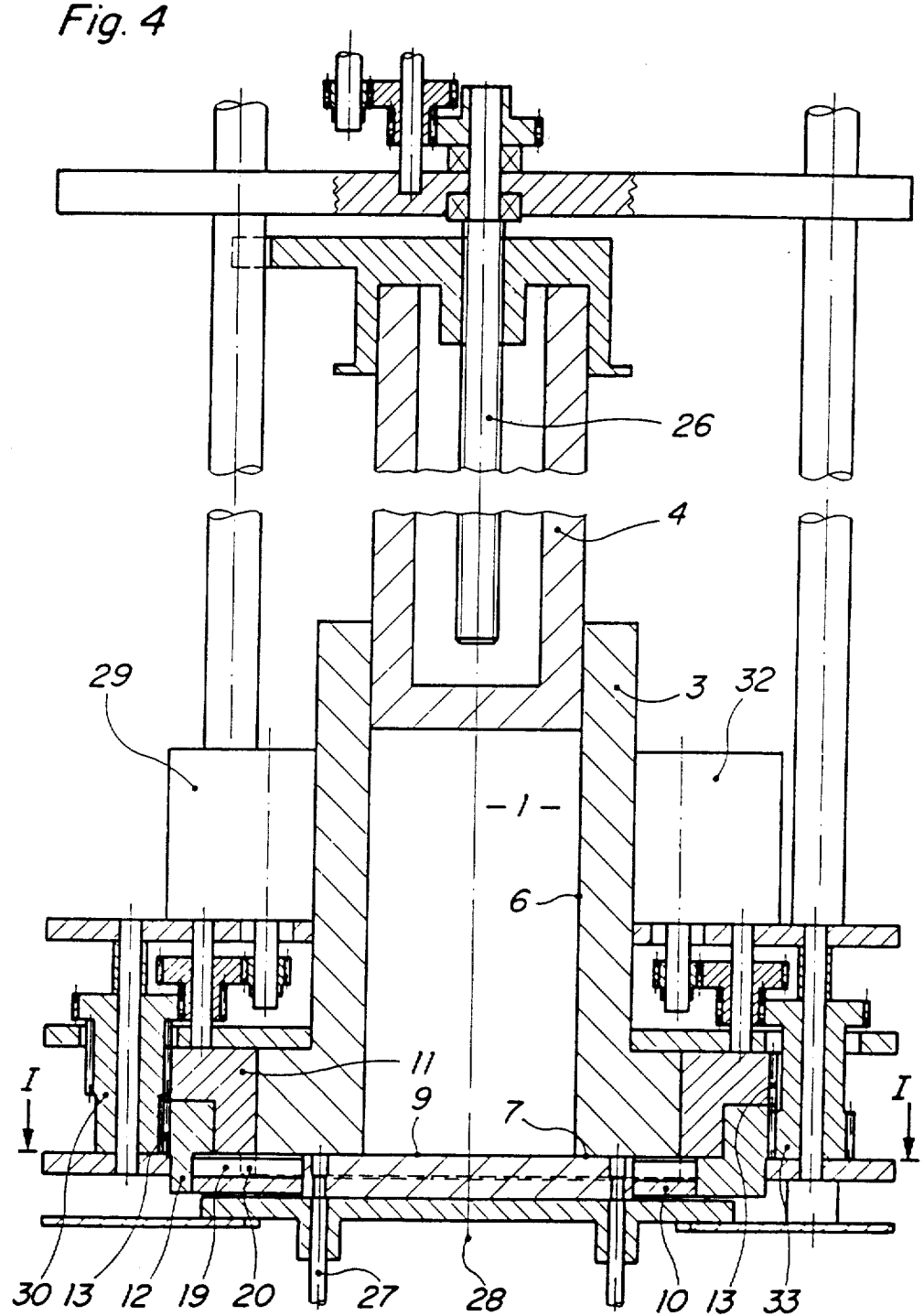
Figure 9:
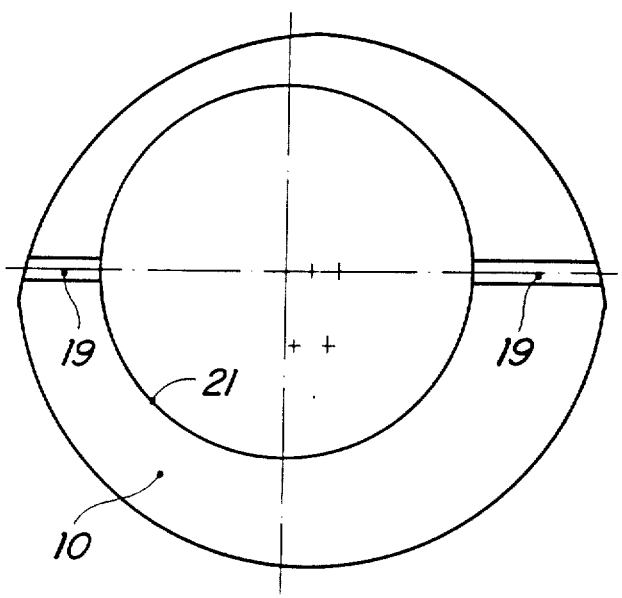
Figure 10:
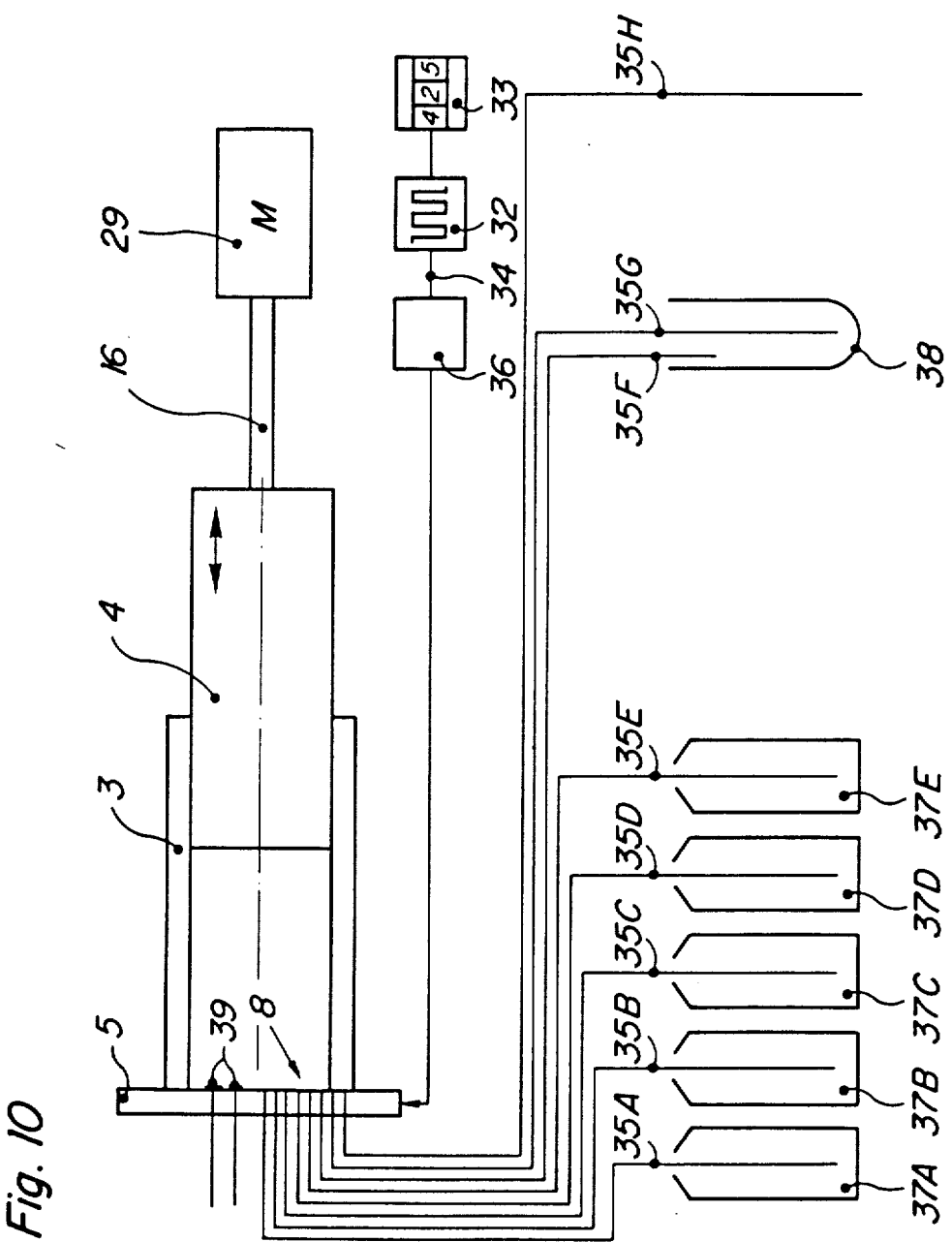
Figure 11:
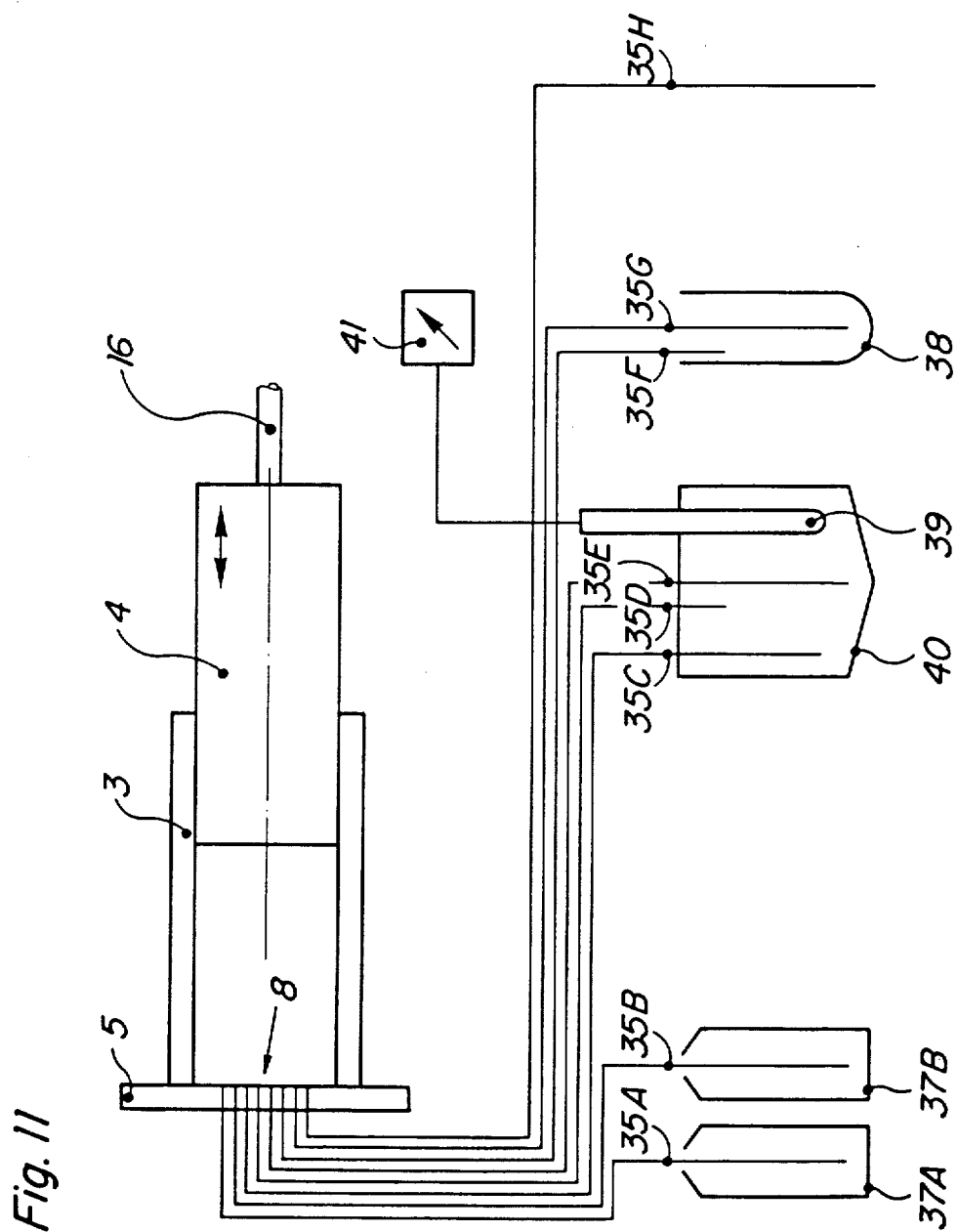

Embodiments of the invention are described in greater detail hereinafter and illustrated in the drawings in which:

FIG. 1 shows an embodiment with a cylinder end portion which is displaceable in a planar manner, FIG. 2 shows an embodiment with an angled piston and a cylinder end portion which is displaceable about the axis of the cylinder, FIG. 3 shows an embodiment having a rotary spool on the cylinder end portion, in which spool is displaceable transversely with respect to the axis of the cylinder, FIG. 4 is a view in cross section through a preferred embodiment of an apparatus, FIGS. 5 through 8 are views in cross section on plane I—I in FIG. 4, in different positions of the circular disc, FIG. 9 is a plan view of the control disc shown in FIG. 4, FIG. 10 is a diagrammatic view of use of an apparatus according to the invention as a reaction cell, FIG. 11 is a diagrammatic view of use of an apparatus according to the invention with a separate reaction cell.

FIGS. 1 to 3 show various possible embodiments of an apparatus according to the invention, many modifications or intermediate forms or even combinations being conceivable. The embodiment shown in FIG. 1 corresponds in principle to the mode of operation shown in FIGS. 4 through 9. The chamber 1 is defined by a cylinder 3, a displaceable piston 4 and a cylinder end portion 5. The cylinder end portion 5 bears sealingly against the end face of the cylinder 3 and is displaceable relative to the cylinder. Disposed in the cylinder end portion 5 are for example two ducts 2a and 2b which can be closed by the end face 7. It will be seen that the end face 7 in combination with the cylinder end portion 5 acts directly as a shut-off or closure member; when the shut-off member is actuated, no residual volume remains in the chamber, which could not be emptied out by the piston 4. FIG. 1a shows the cylinder end portion 5 in a position in which the duct 2b is connected to the chamber 1. In FIG. 1b the cylinder end portion 5 is in a neutral middle position in which both ducts 2a and 2b are closed by the end face 7. The pistion 4 bears against the cylinder end portion 5 so that the chamber volume is equal to zero, without any residual amount remaining behind. In FIG. 1c the duct 2a is in communication with the chamber while the duct 2b is closed.

In practice, FIG. 1 could represent for example a measuring procedure in that in FIG. 1 the chamber is rinsed with a cleaning solution by way of the duct 2b. The cleaning solution is then removed completely from the chamber by way of the duct 2b, by pressing the piston 4 downwardly, whereafter the duct 2b is closed off, as shown in FIG. 1b. Then, as shown in FIG. 1c, starting from a zero chamber volume, a given amount of a liquid is sucked into the chamber 1 by way of the duct 2a. It will be seen that the cylinder end portion 5 may include a plurality of ducts which can be communicated with the chamber 1 in a given or any desired sequence. In that respect the cylinder end portion 5 does not necessarily have to be in the form of a disc. The cylinder end portion also does not necessarily have to be flat. It would also be possible for the surface of the cylinder end portion 5 to be of a part-spherical configuration, in which case it will be appreciated that the end face 7 and the lower boundary face of the piston 4 would also have to be of the same part-spherical shape.

FIG. 2 shows an embodiment in which the ducts 2 are not provided at the cylinder end portion but at the cylinder casing or peripheral portion 6. The volume of the chamber 1 is defined by the inside wall surface of the cylinder casing 6 and by the boundary surface of an angled piston 14 and an end plug portion 15. The plug portion 15 is non-rotatably connected to the piston rod 16 and can thus be rotated about the axis of the cylinder, together with the angled piston 14. When the angled piston 14 is in a condition of bearing completely against the plug portion 15, the volume of the chamber is equal to zero. FIG. 2a shows a position in which the duct 2a is communicated with the chamber. In that position the upper part of the plug portion 15 covers the duct 2b which is in opposite relationship to the duct 2a. FIG. 2b shows a position in which the arrangement consisting of the angled piston 14 and the plug portion 15 have been rotated through 180°. It will be seen that in that position the duct 2a is closed while the duct 2b is communicated with the chamber 1. It will be appreciated that the ducts must be arranged in such a way that in relation to each duct, the volume of the chamber can be reduced to zero. It will be seen that in this embodiment also more than two ducts may be connected to the chamber.

Finally FIG. 3 shows an embodiment in which a rotary spool 17 is arranged on the cylinder end portion 5 of the cylinder 3. The spool 17 is rotatable about an axis which extends transversely with respect to the axis of the cylinder. FIG. 3b shows a view in partial section through FIG. 3a. The rotary spool 17 projects with a given portion thereof into the chamber 1 and thus forms a part of the internal surface defining the chamber. The two ducts 2a and 2b are arranged in the rotary spool 17 in such a way that in a neutral position both ducts are covered by the cylinder end portion 5. By rotating the spool 17 in one direction or the other, either the duct 2a or the duct 2b can be communicated with the chamber 1. In order to permit the volume of the chamber to be reduced to zero, it will be seen that the piston 4 must have a recess 18 therein, which corresponds to the part of the spool 17 that projects into the chamber 1. In this embodiment also the rotary spool 17 may be provided with a plurality of juxtaposed ducts 2.

FIG. 4 is a detail view of a preferred embodiment of the invention in which the cylinder end portion is positioned and displaced by way of a motor drive. The main features of the metering apparatus shown in FIG. 4 are once again the cylinder 3 with a piston 4 displaceable therein, and the cylinder end portion which is formed as a circular disc 9. The piston 4 is displaceable by a motor (not shown), by way of a spindle 26. The relative position of the piston is expressed and indicated in known fashion as a given volume in the chamber 1.

In its lower region the cylinder casing 6 has a somewhat wider wall portion so that the end face 7 of the cylinder casing 6 is somewhat wider than the remainder of the cylinder casing. The circular disc 9 is fluid-tightly pressed against the end face 7. Due to the fine machining of the sealing surfaces, the circular disc 9 is held against the end face 7 just solely by adhesion forces. However, the circular disc 9 may additionally be pressed against the end face 7 by means of a spring force, depending on the respective internal pressures to be expected in the chamber 1.

Figure 5:
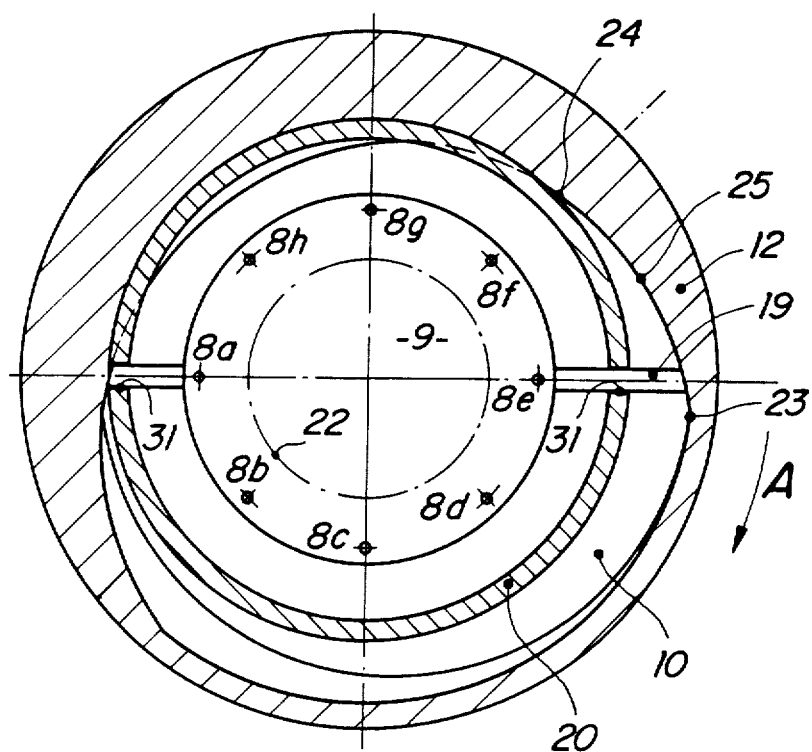
Figure 6:
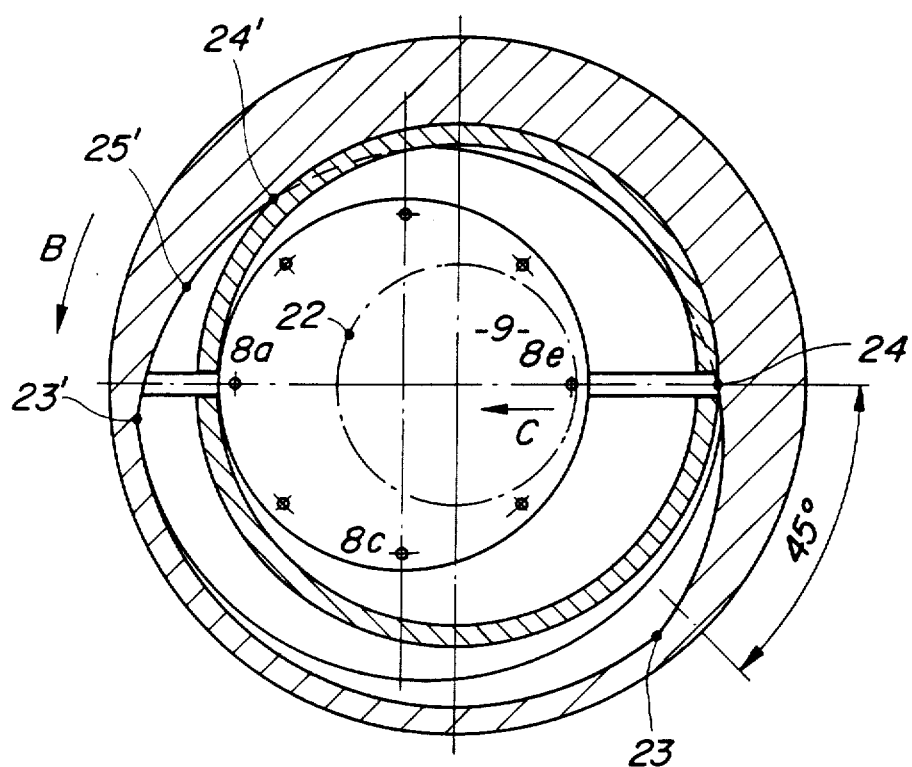

As can be seen in particular from FIG. 5, in its peripheral region the circular disc 9 is provided with eight uniformly angularly distributed openings 8a through 8h, each opening being connected to a separate pipe or hose 27.

The circular disc 9 is disposed in plane-parallel relationship in a control disc 10 which is shown separately in FIG. 9 for the sake of enhanced clarity. The control disc 10 has a bore 12 into which the circular disc 9 fits in such a way as to be rotatable therein. A rib 19 is arranged on the control disc 10 on both sides of the bore 21, on a line which passes through the center of the bore 21 and the circular disc 9.

Arranged above the control disc 10 is a rotary ring 11 which is rotatable about the axis 28 of the cylinder. The rotary ring 11 is mounted directly on the cylinder 3 and is provided with an external tooth configuration as shown at 13. The rotary ring 11 can be driven by means of the motor 29 by way of a gear 30. The rotary ring 11 is provided at its underside with an entrainment tube 20 which has two mutually diametrally oppositely disposed grooves 31.

The ribs 19 of the control disc 10 engage into the grooves 31 in the entrainment tube 20. It will be seen that in that way the control disc 10 is non-rotatably connected to the rotary ring 11, although the control disc 10 can be displaced relative to the rotary ring 11, along the axis defined by the ribs 19. That displaceability of the control disc 10 relative to the rotary ring 11 is a necessary condition in order for the circular disc 9 to be moved from a neutral middle position in which the openings are closed into an open position, as will be further referred to hereinafter.

The control disc 10 is engaged at its outer region by a wedge-action or cam-type disc 12 which, like the rotary ring 11, can also be rotated about the axis of the cylinder. As shown in FIG. 4, for that purpose the disc 12 is rotatably mounted directly on the lower region of the rotary ring 11. The region of the disc 12 which is not of a rotationally symmetrical configuration is shown in FIGS. 5 through 8 as a hatched area. The disc 12 also has an external tooth configuration as indicated at 13 and can be driven in rotation by way of a separate motor 32 and a gear. As the external tooth configuration on the rotary ring 11 and that on the disc 12 preferably have the same number of teeth and the same nominal diameter, it will be appreciated that it is also possible to use only a single drive motor and to provide for the selective of the rotary ring 11 and the disc 12 by way of a displaceable gear.

The mode of operation of the apparatus will now be described in greater detail in particular with reference to FIGS. 5 through 8. In FIG. 5, the cylinder bore 22 is shown by a dash-dotted line. As in FIG. 4, the circular disc 9 is arranged in a neutral position in which all the openings 8a through 8h are outside the cylinder bore 22 and are thus closed by the end face 7 of the cylinder casing 6. If now the opening 8e is to be connected to the chamber, the disc 12 is rotated in the direction indicated by the arrow A while the rotary ring 11 and the entrainment tube 20 are stopped. Upon such rotary movement, a wedge portion 25 which begins at the position indicated at 23 and terminates at the position indicated at 24 applies a force to the control disc 10. Because the entrainment tube 20 is stationary, the control disc 10 can only be deflected in the direction indicated by the arrow C so that, together with the circular disc, it is moved into the position shown in FIG. 6. When that occurs the opening 8e passes into the region of the cylinder bore 22 so that a liquid can be sucked in or ejected by way of that opening. The disc 12 performs a rotary movement through about 45° in order to achieve the open position.

The disc 12 is rotated in the direction indicated by the arrow at B for returning the arrangement to the neutral closure position. When that occurs, a wedge portion 25′ applies a force to the control disc 10. The rotary movement in the direction indicated by the arrow B is continued until the circular disc 9 is restored to the position shown in FIG. 5.

Figure 7:
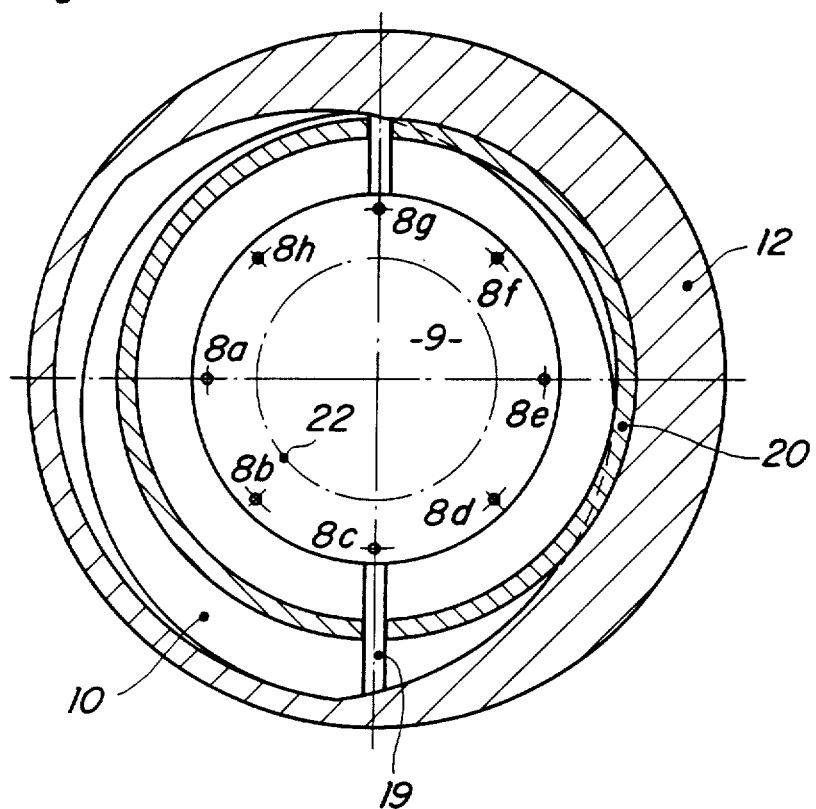
Figure 8:
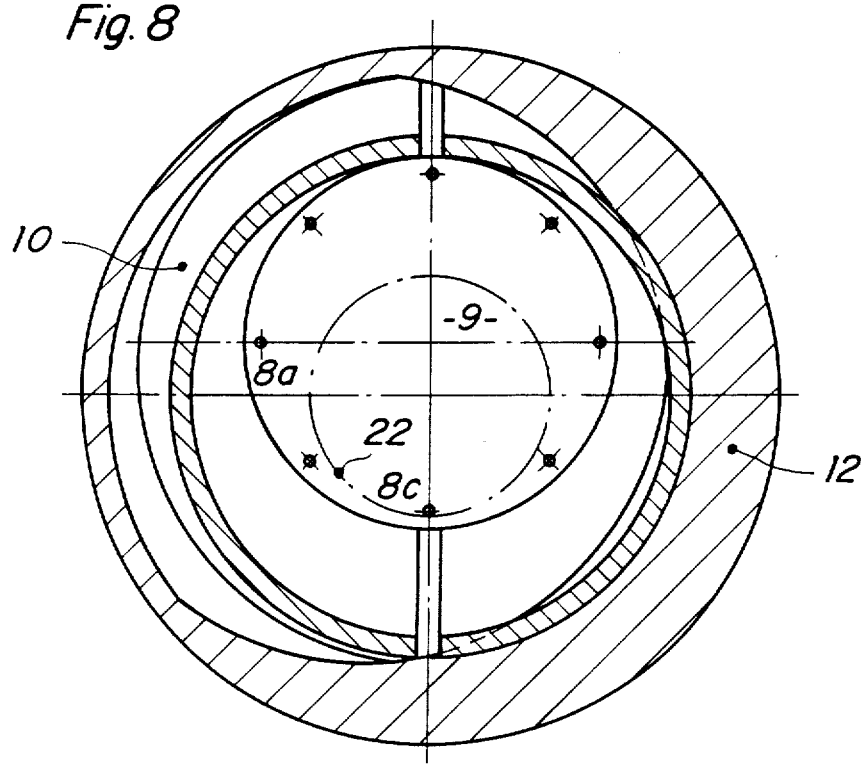

If now for example the opening 8c is to be connected to the chamber 1, then the rotary ring 11 with the entrainment tube 20, the disc 12 and the control disc 10 are rotated about the circular disc 9 or about the axis 28 of the cylinder, until they occupy the position shown in FIG. 7. When that movement occurs the circular disc 9 does not change in its relative position, but it remains immobile against the end face 7 of the cylinder casing 6. As soon as the axis of the rib 19 coincides with the desired line of movement of the circular disc 9, the rotary ring 11 or the entrainment tube 20 is stopped and fixed. The disc 12 is then actuated again so that the control disc 10, with the circular disc 9, is displaced in the manner already described above. As however the relative position of the control disc 10 with respect to the circular disc 9 has altered through 90°, it is now not the opening 8e but the opening 8c that is moved into the region of the cylinder bore 22 and thus communicated with the chamber. In the same manner, each of the openings 8a through 8h may be communicated with the chamber, in any sequence. In that way, it is possible for various liquids to be introduced into or removed from the chamber, in precise quantities, in an extremely simple and accurate fashion.

Practical use of the apparatus in a measuring arrangement will be described hereinafter with reference to FIGS. 10 and 11.

Referring to FIG. 10, a metering cylinder 3 is provided with a piston 4 which is displaceable in the metering cylinder 3 by means of a drive element 29, by predeterminable proportions by volume or by proportions by volume which are dependent on the measurement value. The drive element 29, for example a linear motor, is activated in known fashion by a control device which is connected to a counter and preselection means 33. The control device supplies pulses to the drive element in known manner, the pulses causing a movement of a piston rod 16 and thus the piston 4, which is proportional to the number of pulses. By preselection, the number of pulses to be supplied by the control device 32 and thus the displacement of the drive element 29 can be adjusted by means of the counter 33. As the displacement of the piston rod 16 by the drive element is proportional to the change in volume in the metering cylinder 3, a desired change in volume can be preset in that way at the counter 33. Alternatively it is also possible to activate the control device 32 and in that way, by suitable displacement of the drive element 29 and the piston rod 16, to produce a change in volume and to read off the change in volume at the counter 33. That method is used for example when a titration operation is carried out in the metering cylinder 3. For the purposes of introducing solutions, the cylinder end portion 5 of the metering cylinder 3 has eight different feed line connections or openings 8 for the lines 35A through 35H. The shut-off member is actuated, for opening or closing the openings 8, by the valve control means 36. The valve control means 36 is also connected to the control device 32 by a connecting line 34. Control pulses are supplied to the control device 32 by way of the connecting line 34, those pulses providing that the drive element 29 is activated only when one of the openings 8 is opened by the valve control means 36. The feed lines 35A through 35E are supplied with reagents and auxiliary solutions, from containers 37A through 37E which are shown in diagrammatic form. The feed lines 35F and 35G are connected to a measuring solution container 38. A waste line 35H goes into a waste container (not shown).

In order to analyze measurement solution in the container 38, for example by titration, the arrangement is operated in the following manner:

First of all, the opening connected to the waste line 35H is opened by the valve control means 36. The control device 32 is then activated in order to displace the piston 4 until it comes into a condition of abutment, towards the left. When that occurs, the solution mixture in the metering cylinder 3 is ejected by way of the line 35H. The opening connected to the waste line 35H is then closed again. In order to clean the metering cylinder, the openng connected to the line 35A is them opened by the valve control means 36, the drive element 29 is activated by the control device and cleaning solution is sucked into the metering cylinder 3 from the container 37A by suitable displacement of the piston 4. The opening in the line 35A is closed again and the opening in the line 35H is opened so that the cleaning solution can be forced out by displacement of the piston 4 into the left-hand position.

The opening in the line 35H is then closed again and the opening in the line 35G is opened. The desired amount by volume can then be preselected at the counter and preselector means 33, whereupon the control device 32 activates the drive element 29 and, by displacing the piston 4, produces an increase in the volume in the metering cylinder 3, by the desired amount. When that occurs, the desired amount of solution is sucked in from the container 38. The opening associated with the line 35G is then closed and the opening in the line 35B is opened. The cylinder 37B contains an auxialiary solution which is suitable for the titration operation to be carried out. The control device 32 is then activated continuously or in indivudial steps until a suitable change in measurement value of the sensors is to be observed in the metering cylinder 3 in known manner. The control device 32 is then switched off, while the amount of auxiliary solution which was sucked in until reaction occurs, by way of the line 35B, can be read off at the counter 33.

In order to accelerate mixing of the liquids in the chamber, a rotary or vibratory member may be disposed on or in the chamber. In that respect, a dead volume should be avoided, in a similar fashion as in relation to the sensors. Thus it would be possible for example for the piston itself to be caused to rotate and/or pulsate.

The containers 37C through E are provided for further auxiliary solutions, in carrying out multi-stage processes. For example in the course of the operating procedure cleaning solution may be sucked into the metering cylinder 3 from the container 37A and then sprayed into the container 38 by way of the line 35F so that the latter is cleaned. The container 3B is then sucked out again by way of the line 35G and then, by means of suitable valve actuation, the cleaning solution is passed by way of the line 35H to the waste container (not shown).

As diagrammatically indicated, two ion-sensitive electrodes are arranged as sensors in the cylinder end portion 5 at 39. The electrodes 39 are provided for determining the ion content in per se known manner. The electrodes are flush with the inside wall surface of the cylinder end portion so that no dead space is formed when emptying the metering cylinder 3. The electrode 39 are connected to an evaluation circuit (not shown). It will be seen that it is possible to carry out an extremely precise ion content analysis operation in the metering cylinder 3 in a very simple manner. Precisely predeterminable amounts of measurement solution and reagents or auxiliary solutions can be sucked in sequentially and without additional metering means, such as for example burettes, and analyzed directly in the metering cylinder 3.

It will be appreciated that the ion-sensitive electrodes 39 may be replaced by any other sensors, depending on what type of reaction of analysis operation is to be carried out in the metering cylinder 3.

FIG. 11 shows a modified embodiment in which the movement of the piston rod 16 and actuation of the shut-off member occur in identical fashion to the embodiment shown in FIG. 10. The valve control means 36, the control device 32 and the counter and preselector means 33 as well as the drive element 29 are therefore not shown for the sake of clarity of the drawing. The embodiment shown in FIG. 11 has only two containers 37A and 37B for reagents and auxiliary solutions, in which the solution to be analyzed is disposed. Unlike the embodiment shown in FIG. 10, the FIG. 11 embodiment additionally has a reaction or measurement cell 40 which is connected to the metering cylinder 3 by way of lines 35C, 35D and 35E. For the purposes of metering the solution to be measured and auxiliary solutions, the desired mixture is sucked in in the same way as in the embodiment shown in FIG. 10, by suitable sequential actuation of the shut-off member and a simultaneous increase in the volume of the metering cylinder 3, by displacement of the piston 4. Thereafter however the content of the metering cylinder 3 is ejected into the reaction measurement cell 40 by way of the line 35C, after the appropriate opening has been opened, and it is then analyzed in the cell 40 by means of a sensor 39 and an evaluation means 41.

It will be seen that the arrangement shown in FIG. 10 may also be combined with an arrangement as shown in FIG. 11. Thus for example various sensors may be disposed in the cylinder end portion 5 for given analysis operations. The solutions may then be analyzed directly in the metering cylinder 3 in the above-described manner by means of those sensors. If in addition a further analysis operation is to be carried out, for which the installed electrodes 39 are not suited, then an additional reaction measurement cell 40 may be connected to the metering cylinder 3.

We claim:

1. An apparatus for the qualitative and quantitative analysis of liquids, comprising means defining a chamber for receiving liquids, adjustable means for varying the volume of the chamber, the means defining the chamber including at least two ducts capable of opening into the chamber for feeding and dischanging the liquids, the means defining the chamber comprising at least two wall portions, one of the wall portions being displaceable relative to the other wall portion independently of the adjustment of the means for varying the chamber volume, the at least two ducts arranged in one of the wall portions, shut-off means for closing and opening the ducts capable of opening into the chamber, the shut-off means being formed in one of the wall portions by a single surface area facing the ducts, the shut-off means and the one wall in which the at least two ducts are arranged being displaceable relative to each other between first and second positions, at least one of the at least two ducts being closed by the shut-off means in the first position with another of the at least two ducts opening into the chamber, while in the second position, the at least one of the ducts opens into the chamber with the another of the ducts being closed by the shut-off means whereby the liquids in the chamber can be ejected fully through one of the at least two ducts while the another of the at least two ducts is not in communication with the chamber, one of the two wall portions being a cylinder having an end face, and the means for varying the volume of the chamber being a piston slidably received in the cylinder, wherein the displaceable wall portion is a cylinder end member facing the end face of the cylinder, the ducts capable of opening into the chamber being arranged in the displaceable wall portion at the end of the cylinder, the cylinder end member forming the displaceable wall portion bearing sealingly against the end face of the cylinder, the ducts in the displaceable wall portion defining openings in the surface area of the wall portion facing the interior of the chamber, and the openings being closeable by the end face of the cylinder, a plurality of separate ducts defining openings being arranged so as to be located in a circle in the cylinder end member, such that all openings are closeable by the end face of the cylinder, and that at least one opening can be opened by displacing the cylinder end member relative to the longitudinal axis of the cylinder, wherein the cylinder end member is a circular disc comprising a control disc in which the circular disc is disposed in a plane-parallel relationship in such a way that the control disc is rotatable about the circular disc, a rotary ring to which the control disc is connected in such a way that the control disc is not rotatable relative to the rotary ring, but is displaceable in the plane of the circular disc, a wedge-action disc engaging the control disc for displacing the control disc together with the circular disc, the wedge-action disc being rotatable about the axis of the cylinder together with the rotary ring for positioning the control disc, and the wedge-action disc being rotatable about the axis of the cylinder while the rotary ring remains stationary for displacing the circular disc.

* * * * *

UNITED STATES PATENT AND TRADEMARK OFFICE
CERTIFICATE OF CORRECTION

PATENT NO. : 4,715,237
DATED : December 29, 1987
INVENTOR(S) : Karl Kaempf et al It is certified that error appears in the above-identified patent and that said Letters Patent is hereby corrected as shown below:

In the heading of the Patent, it should read:

[21]　Appl. No.: 848,404

Signed and Sealed this

Twenty-first Day of June, 1988

Attest:

DONALD J. QUIGG

*Attesting Officer*　　　*Commissioner of Patents and Trademarks*